US011969461B2

(12) United States Patent
Fink et al.

(10) Patent No.: US 11,969,461 B2
(45) Date of Patent: Apr. 30, 2024

(54) COMPOSITION COMPRISING BOTULINUM TOXIN

(71) Applicant: MERZ PHARMA GMBH & CO. KGAA, Frankfurt am Main (DE)

(72) Inventors: Klaus Fink, Cologne (DE); Harold Taylor, Frankfurt am Main (DE); Hermann Russ, Altendorf SZ (CH); Peter Boderke, Schwalbach (DE)

(73) Assignee: MERZ PHARMA GMBH & CO. KGAA, Frankfurt am Main (DE)

(*) Notice: Subject to any disclaimer, the term of this patent is extended or adjusted under 35 U.S.C. 154(b) by 416 days.

(21) Appl. No.: 16/079,367

(22) PCT Filed: Feb. 28, 2017

(86) PCT No.: PCT/EP2017/054596
§ 371 (c)(1),
(2) Date: Aug. 23, 2018

(87) PCT Pub. No.: WO2017/148915
PCT Pub. Date: Sep. 8, 2017

(65) Prior Publication Data
US 2019/0060422 A1  Feb. 28, 2019

(30) Foreign Application Priority Data
Mar. 2, 2016 (EP) .................................... 16158302

(51) Int. Cl.
| A61K 8/64 | (2006.01) |
| A61K 8/73 | (2006.01) |
| A61K 9/00 | (2006.01) |
| A61K 9/08 | (2006.01) |
| A61K 38/48 | (2006.01) |
| A61K 47/36 | (2006.01) |
| A61P 21/00 | (2006.01) |
| A61Q 19/08 | (2006.01) |

(52) U.S. Cl.
CPC ............ *A61K 38/4893* (2013.01); *A61K 8/64* (2013.01); *A61K 8/735* (2013.01); *A61K 9/0019* (2013.01); *A61K 9/08* (2013.01); *A61K 47/36* (2013.01); *A61P 21/00* (2018.01); *A61Q 19/08* (2013.01); *A61K 2800/91* (2013.01)

(58) Field of Classification Search
CPC .... A61K 38/4893; A61K 9/08; A61K 9/0019; A61K 8/64; A61K 8/735; A61K 47/36; A61K 2800/91; A61K 9/19; A61K 31/728; A61P 21/00; A61P 17/00; A61Q 19/08

See application file for complete search history.

(56) References Cited

U.S. PATENT DOCUMENTS

| 6,903,187 | B1 | 6/2005 | Steward et al. | |
|---|---|---|---|---|
| 7,491,799 | B2 | 2/2009 | Steward et al. | |
| 8,444,991 | B2 | 5/2013 | Randolph et al. | |
| 8,563,521 | B2 | 10/2013 | Skerra et al. | |
| 8,748,151 | B2 | 6/2014 | Frevert | |
| 8,808,710 | B2 | 8/2014 | Randolph et al. | |
| 9,050,246 | B2 | 6/2015 | Bertholon et al. | |
| 9,050,336 | B2 * | 6/2015 | Blanda ................... | A61K 47/36 |
| 9,161,970 | B2 * | 10/2015 | Tezel ..................... | A61Q 19/08 |
| 9,260,494 | B2 | 2/2016 | Skerra et al. | |
| 9,388,394 | B2 | 7/2016 | Heinrichs et al. | |
| 9,622,957 | B2 * | 4/2017 | Tezel ....................... | A61K 8/64 |
| 9,758,573 | B2 | 9/2017 | Vartanian et al. | |
| 9,809,809 | B2 | 11/2017 | Schmidt et al. | |
| 9,827,298 | B2 | 11/2017 | Hofmann et al. | |
| 9,975,929 | B2 | 5/2018 | Frevert et al. | |
| 10,022,424 | B2 | 7/2018 | Stossel et al. | |
| 2002/0127247 | A1 | 9/2002 | Steward et al. | |
| 2009/0155314 | A1 | 6/2009 | Tezel et al. | |
| 2010/0172940 | A1 | 7/2010 | Petrella | |
| 2012/0135937 | A1 | 5/2012 | Bertholon et al. | |
| 2012/0141532 | A1 | 6/2012 | Blanda et al. | |
| 2012/0295914 | A1 | 11/2012 | Villard | |
| 2013/0165389 | A1 | 6/2013 | Schellenberger et al. | |
| 2015/0044250 | A1 | 2/2015 | Heinrichs et al. | |
| 2015/0320743 | A1 | 11/2015 | Bertholon et al. | |
| 2015/0322118 | A1 | 11/2015 | Groer et al. | |
| 2017/0058006 | A1 | 3/2017 | Frevert et al. | |

(Continued)

FOREIGN PATENT DOCUMENTS

| EP | 2369005 | 9/2011 |
|---|---|---|
| EP | 3335719 | 6/2018 |

(Continued)

OTHER PUBLICATIONS

Tosoh Application Note, Analysis of Hyaluronic Acid Using the EcoSEC GPC System, 2020, https://www.ecosec.eu// SharedTBGFileLibrary/TBG/Products%20Download/Application% 20Note/a17i17a.pdf, 1-3 (Year: 2020).*
Kukreja, R. et al. The botulinum toxin as a therapeutic agent: molecular and pharmacological insights, 2015, Research and Reports in Biochemistry, 173-183 (Year: 2015).*
Owen, S. et al. Hyaluronic Acid, 2017, Comprehensive Biomaterials II, Chapter 2.14, 306-331 (Year: 2017).*
Gupta, R. et al. Hyaluronic Acid: Molecular Mechanisms and Therapeutic Trajectory, 2019, Frontiers in Veterinary Science, 1-24 (Year: 2019).*
Papakonstantinou, E. et al. Hyaluronic acid, 2012, Dermato-Endocrinology, 4(3): 253-258 (Year: 2012).*

(Continued)

Primary Examiner — Louise W Humphrey
Assistant Examiner — Anjali Ajit Hirani
(74) Attorney, Agent, or Firm — Leydig, Voit & Mayer, Ltd.

(57) ABSTRACT

The present invention concerns a composition comprising (a) botulinum toxin and (b) non-crosslinked hyaluronic acid and its use of the treatment or prevention of dystonia, spasticity and/or wrinkles. Further, the present invention relates to a method for cosmetically smoothing or preventing wrinkles comprising the step of administering the present composition.

13 Claims, 2 Drawing Sheets

(56) References Cited

U.S. PATENT DOCUMENTS

| | | |
|---|---|---|
| 2018/0141982 A1 | 5/2018 | Anderson et al. |
| 2018/0169182 A1 | 6/2018 | Frevert et al. |
| 2018/0327730 A1 | 11/2018 | Hofmann et al. |
| 2020/0048624 A1 | 2/2020 | Hofmann et al. |
| 2020/0129587 A1 | 4/2020 | Frevert et al. |
| 2020/0131494 A1 | 4/2020 | Frevert et al. |
| 2020/0354706 A1 | 11/2020 | Frevert et al. |
| 2021/0008156 A1 | 1/2021 | Frevert et al. |

FOREIGN PATENT DOCUMENTS

| | | |
|---|---|---|
| EP | 3649143 | 5/2020 |
| RU | 2530604 C2 | 7/2013 |
| WO | WO 1995/032738 | 12/1995 |
| WO | WO 1996/039166 | 12/1996 |
| WO | WO 2000/012728 | 3/2000 |
| WO | WO 2001/014570 | 3/2001 |
| WO | WO 2002/008268 | 1/2002 |
| WO | WO 2002/040506 | 5/2002 |
| WO | WO 2005/007185 | 1/2005 |
| WO | WO 2005/068494 | 7/2005 |
| WO | WO 2006/017749 | 2/2006 |
| WO | WO 2006/020208 | 2/2006 |
| WO | WO 2006/076902 | 7/2006 |
| WO | WO 2008/155134 | 12/2008 |
| WO | WO 2009/114748 | 9/2009 |
| WO | 2010028025 A1 | 3/2010 |
| WO | WO 2010/091122 | 8/2010 |
| WO | 2010136585 A2 | 12/2010 |
| WO | 2010136594 A2 | 12/2010 |
| WO | 2011109130 A1 | 9/2011 |
| WO | WO 2011/123813 | 10/2011 |
| WO | WO 2011/144756 | 11/2011 |
| WO | 2012052562 A1 | 4/2012 |
| WO | WO 2013/049508 | 4/2013 |
| WO | WO 2013/068472 | 5/2013 |
| WO | WO 2013/068476 | 5/2013 |
| WO | WO 2013/082116 | 6/2013 |
| WO | WO 2013/112867 | 8/2013 |
| WO | WO 2014/068317 | 5/2014 |
| WO | WO 2014/086494 | 6/2014 |
| WO | WO 2014/207109 | 12/2014 |
| WO | WO 2015/132004 | 9/2015 |
| WO | WO 2015/183044 | 12/2015 |
| WO | WO 2016/025626 | 2/2016 |
| WO | WO 2016/073562 | 5/2016 |
| WO | WO 2016/110662 | 7/2016 |
| WO | WO 2016/180533 | 11/2016 |
| WO | WO 2016/198163 | 12/2016 |
| WO | WO 2017/125487 | 7/2017 |
| WO | WO 2018/233813 | 12/2018 |
| WO | WO 2019/007509 | 1/2019 |
| WO | WO 2019/081022 | 5/2019 |
| WO | WO 2019/101308 | 5/2019 |
| WO | WO 2020/088667 | 5/2020 |

OTHER PUBLICATIONS

Cowman, M. et al. Viscoelastic Properties of Hyaluronan in Physiological Conditions, 2015, F1000 Research, 4(622): 1-13 (Year: 2015).*

A.S. Kolbin et al. "Pharmacoepidemiology of botulinum toxin preparations incomprehensive post-stroke spasticity therapy in the Russian Federation: Survey data from neurologists" Kachestvennaya Klinicheskaya Praktika, (2014) 13 pages.

Ganceviciene, Ruta, et al. "Skin anti-aging strategies." Dermatoendocrinology 4.3 (2012): 308-319.

International Search Report and Written Opinion in corresponding International Patent Application No. PCT/EP2017/054596, dated May 23, 2017. 9 pages.

International Preliminary Report on Patentability in corresponding International Patent Application No. PCT/EP2017/054596, dated Sep. 4, 2018. 7 pages.

Altschul et al. (1990) "Basic local alignment search tool," J. Mol. Bio. 215(3): 403-410.

Aoki (2001) "A comparison of the safety margins of botulinum neurotoxin serotypes A, B, and F in mice," Toxicon 39: 1815-1820.

Arndt et al. (2006) "A Structural Perspective of the Sequence Variability Within Botulinum Neurotoxin Subtypes A1-A4," Journal of Molecular Biology 362(4): 733-742.

Band et al. (2010) "Recombinant derivatives of botulinum neurotoxin A engineered for trafficking studies and neuronal delivery," Protein Expression and Purification, Academic Press 71(1): 62-73.

Binz et al. (2018) Abstract for "Mutations in Light Chain of Botulinum Neurotoxin A Enable Cleavage of Human SNAP-23," Abstracts/Toxicon 156: p. S10.

"Botulinum neurotoxin type E non-toxic component," (1993) available online at https://www.ncbi.nlm.nih.gov/protein/p46082, accessed Dec. 2017.

"BPXTEN construction related XTEN polypeptide sequence Seq ID 767," XP002776714, retrieved from EBI accession No. Gsp: AYG93920, Database accession No. AYG93920 Sep. 2010, 2 pp.

Breidenbach et al. (2004) "Substrate recognition strategy for botulinum neurotoxin serotype A," Nature 432: 925-929.

Cox (2008) "Botox Jabs: A New Weapon Against Chronic Pain," ABC News, available online at https://abcnews.go.com/Health/PainManagement/story?id=4148566&page=1, 2 pp.

Dressler et al. (2005) "Mouse diaphragm assay for detection of antibodies against botulinum toxin type B," Movement Disorders 20(12): 1617-1619.

European Search Report, dated Aug. 29, 2016, corresponding to European Patent Application No. 16 15 8302.6, 5 pp.

European Office Action, dated Mar. 18, 2020, corresponding to European Patent Application No. 17 707 051.3, 4 pages.

Fan et al. (2015) "Monoclonal Antibodies Targeting the Alpha-Exosite of Botulinum Neurotoxin Serotype/A Inhibit Catalytic Activity," PLoS ONE 10(8): 1-23.

Fernandez-Salas et al. (2004) "Plasma membrane localization signals in the light chain of botulinum neurotoxin," Proc. Natl. Acad. Sci. U.S.A. 101(9): 3208-3213.

Hallis et al. (1996) "Development of novel assays for botulinum type A and B neurotoxins based on their endopeptidase activities," J. Clin. Microbiol. 34(8): 1934-1938.

Higgins et al. (1989) "Fast and sensitive multiple sequence alignments on a microcomputer," CABIOS 5(2): 151-153.

International Preliminary Report on Patentability, dated Jan. 2, 2020, corresponding to International Application No. PCT/EP2017/065096 (filed Jun. 20, 2017), 7 pp.

International Preliminary Report on Patentability, dated Jan. 16, 2020, corresponding to International Application No. PCT/EP2017/066891 (filed Jul. 6, 2017), 9 pp.

International Preliminary Report on Patentability, dated May 7, 2020, corresponding to International Application No. PCT/EP2017/077427 (filed Oct. 28, 2017), 8 pp.

International Preliminary Report on Patentability, dated Jun. 4, 2020, corresponding to International Application No. PCT/EP2017/080117 (filed Nov. 22, 2017), 11 pp.

Jones et al. (2008) "Development of improved SNAP25 endopeptidase immuno-assays for botulinum type A and E toxins," J. of Immunological Methods 329(1-2): 92-101.

Keller (2006) "Recovery from botulinum neurotoxin poisoning in vivo," Neuroscience 139(2): 629-637.

Kumaran et al. (2008) "Substrate Binding Mode and Its implication on Drug Design for Botulinum Neurotoxin A," PLoS Pathogens 4(9): e1000165, pp. 1-9.

Li et al. (1998) "Molecular characterization of type E Clostridium botulinum and comparison to other types of Clostridium botulinum," Biochim. Biophys. Acta. 1395(1):21-27.

Needleman et al. (1970) "A general method applicable to the search for similarities in the amino acid sequence of two proteins," J Mol Biol 48: 443-453.

Pearce et al. (1994) "Measurement of Botulinum Toxin Activity: Evaluation of the Lethality Assay," Toxicol. Appl. Pharmacol. 128(1): 69-77.

Pearson et al. (1988) "Improved tools for biological sequence comparison," PNAS 85(8):2444-2448.

(56) References Cited

OTHER PUBLICATIONS

Ravichandran et al. (2006) "An Initial Assessment of the Systemic Pharmacokinetics of Botulinum Toxin," JPET 318(3):1343-1351.
Schlapschy et al. (2013) "PASylation: a biological alternative to PEGylation for extending the plasma half-life of pharmaceutically active proteins," Protein Engineering, Design and Selection 26(8): 489-501.
Search Report dated May 6, 2015, corresponding to International Application No. PCT/EP2015/000489 (filed Mar. 4, 2015), 4 pp.
Search Report and Written Opinion, dated Sep. 26, 2016, corresponding to International Application No. PCT/EP2016/000962 (filed Jun. 10, 2016), 10 pp.
Search Report and Written Opinion, dated Dec. 1, 2017, corresponding to International Application No. PCT/EP2017/066891 (filed Jul. 6, 2017), 12 pp.
Search Report and Written Opinion, dated Jan. 8, 2018, corresponding to International Application No. PCT/EP2017/065096 (filed Jun. 20, 2017), 10 pp.
Search Report and Written Opinion, dated Feb. 20, 2018, corresponding to International Application No. PCT/EP2017/077427 (filed Oct. 26, 2017), 11 pp.
Search Report and Written Opinion, dated Jun. 18, 2018, corresponding to International Application No. PCT/EP2017/080117 (filed Nov. 22, 2017), 18 pp.
Shao et al. (2019) "Construction of functional chimeras of syntaxin-1A and its yeast orthologue, and their application to the yeast cell-based assay for botulinum neurotoxin serotype C," BBA-General Subjects 1863: 129396, pp. 1-12.
Smith et al. (1981) "Comparison of biosequences," Adv Appl Math 2: 482-489.
Stancombe et al. (Feb. 2012) "Engineering botulinum neurotoxin domains for activation by toxin light chain," Febs Journal 279(3): 515-523.
Third Part Observation for Application No. EP20170707051, dated Sep. 10, 2020, 10 pages.
USPTO Office Action, dated Jun. 29, 2020, corresponding to U.S. Appl. No. 16/498,257, 9 pp.
USPTO Office Action, dated Dec. 10, 2020, corresponding to U.S. Appl. No. 16/498,257, 22 pp.
Vazquez-Cintron et al. (Aug. 2016) "Pre-Clinical Study of a Novel Recombinant Botulinum Neurotoxin Derivative Engineered for Improved Safety," Scientific Reports 6(1), 30429: 1-10.
Wang et al. (2011) "A Dileucine in the Protease of Botulinum Toxin A Underlies Its Long-lived Neuroparalysis," J. Biol. Chem. 286(8): 6375-6385.
Wang et al. (2013) "Comparison of the catalytic properties of the botulinum neurotoxin subtypes A1 and A5," Biochimica et Biophysica Acta 1843: 2722-2728.
Weber (2013) "Inhibierung von Stat5 in Tumoren durch RNA-Interferenz und spezifische Interaktion eines Peptidaptamer-Konstruktes milder DNA-Bindedomane," PhD thesis, Johann-Wolfgang-Goethe Universitat, Frankfurt am Main (Germany), in German language with English translation of Summary (p. XIII-XIV) and Discussion (p. 220).
Xue et al. (2014) "Probing BoNT/A Protease Exosites: Implications for Inhibitor Design and Light Chain Longevity," Biochemistry 53(43): 6820-6824.
U.S. Appl. No. 16/760,377, filed Apr. 29, 2020.
U.S. Appl. No. 16/755,848, filed Apr. 13, 2020.
U.S. Appl. No. 16/498,193, filed Sep. 26, 2019.
U.S. Appl. No. 16/498,257, filed Sep. 26, 2019.
U.S. Appl. No. 17/482,953, filed Sep. 23, 2021.
Arnon et al. (2001) "Botulinum Toxin as a Biological Weapon", *JAMA* 285(8):1059-1570.
Awsare et al. (2020) "Wound Botulism Caused by Botulinum Neurotoxin Type A in a Chromic Parenteral Drug Abuser", *Neurology* 12(3):422-427, DOI: 10.1159/000510846.
Jansen et al. (2014) "Biological warfare, bioterrorism and biocrime", *Clin Micobiol Infect* 20(6):488-496.
Lonati et al. (2020) "Foodborne Botulism Clinical Diagnosis and Medical Treatment", *Toxins* 12:509, DOI:10.3390/toxins12080509.
Simpson et al. (2013) "The life history of a botulinum toxin molecule", *Toxicon* 68:40-59.
Bork, Peer (2000) "Powers and pitfalls in sequence analysis: the 70% hurdle", Genome Research, 10:398-400.
Bowie et al. (1990) "Deciphering the message in protein sequences: tolerance to amino acid substitutions", Science, 247:1306-1310.
Burgess et al. (1990) "Possible dissociation of the heparin-binding and mitogenic activities of heparin-binding (acidic fibroblast) growth factor-1 from its receptor-binding activities by site-directed mutagenesis of a single lysine residue", J. of Cell Bio. 111:2129-2138.
Lazar et al. (1988) "Transforming growth factor alpha: mutation of aspartic acid 47 and leucine 48 results in different biological activities", Mol. Cell Biol. 8:1247-1252.
Skolnick et al. (2000) "From genes to protein structure and function: novel applications of computational approaches in the genomic era", Trends Biotechnol. 18:34-39.

\* cited by examiner

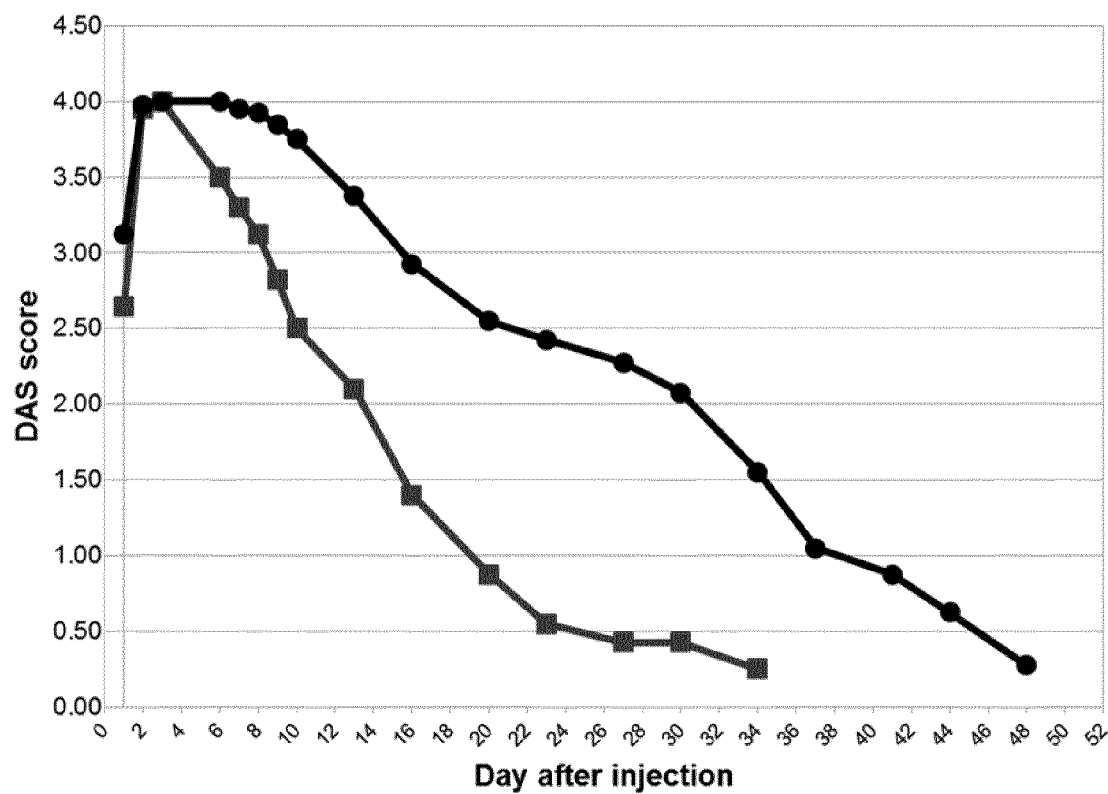
Fig. 1: Digit abduction scoring of mice injected into the right gastrocnemius muscle with 0.8 ml of the composition according to the Reference Example (squares) or with 1.6 ml of the composition according to Example 1 (bullets).

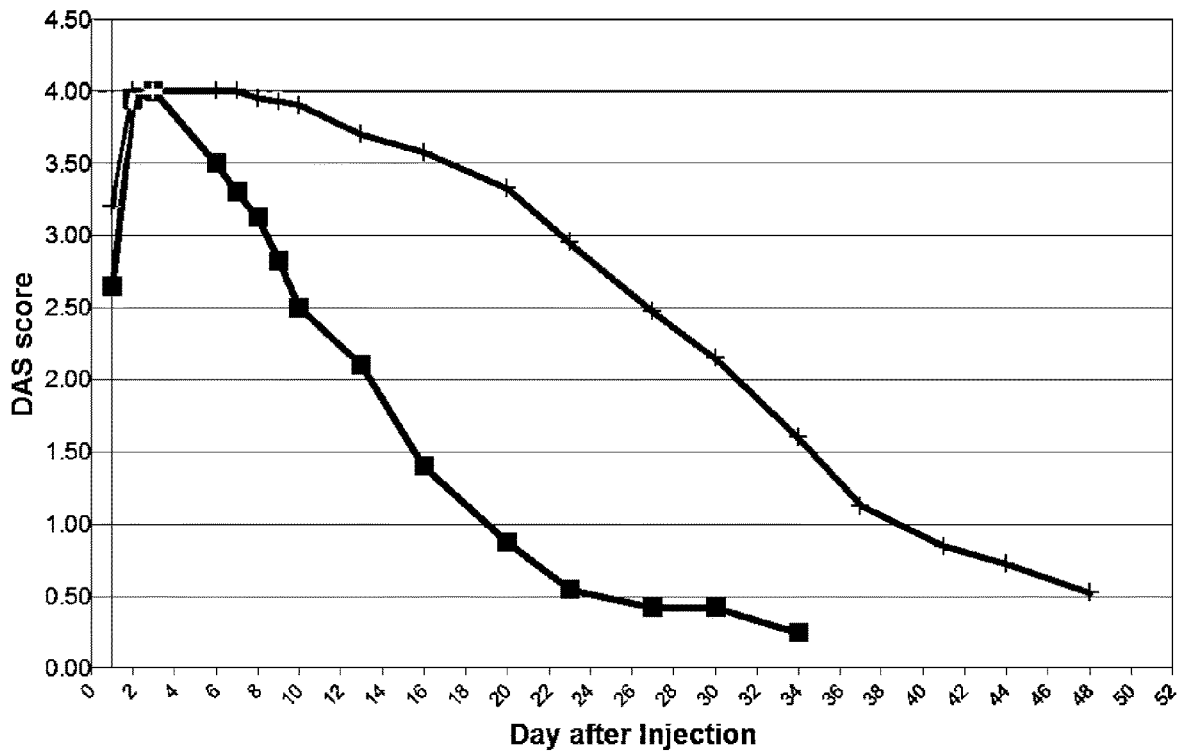
Fig. 2: Digit abduction scoring of mice injected into the right gastrocnemius muscle with 0.8 ml of the composition according to the Reference Example (squares) or with 2.5 ml of the composition according to Example 1 (crosses).

COMPOSITION COMPRISING BOTULINUM TOXIN

CROSS-REFERENCE TO RELATED PATENT APPLICATIONS

This application is a U.S. National Stage Application under 35 U.S.C. § 371 of International Patent Application No. PCT/EP2017/054596, filed Feb. 28, 2017, which claims the benefit of priority under 35 U.S.C. Section 119(e) of European Patent Application number 16158302.6 filed Mar. 2, 2016, both of which are incorporated by reference in their entireties. The International Application was published on Sep. 8, 2017, as International Publication No. WO 2017/148915 A1.

The present invention concerns a composition comprising (a) botulinum toxin and (b) non-crosslinked hyaluronic acid and its use for the treatment or prevention of dystonia, spasticity and/or wrinkles. Further, the present invention relates to a method for cosmetically smoothing or preventing wrinkles comprising the step of administering the present composition.

BACKGROUND

"Botulinum neurotoxin" (BoNT) can be regarded as a general term for a group of several, very similar neurotoxic proteins. The naturally occurring botulinum neurotoxin is produced by an anaerobic and spore-forming bacterium *Clostridium botulinum* and rarely by other *Clostridium* species, such as *C. butyricum, C. barati* and *C. argentinense*. There are currently eight different serotypes of the toxin known as type A, B, $C_1$, $C_2$, D, E, F and G. Some of these types such as A, B, E and F are toxic for human beings while Types C, D and G more often cause toxicity for example in birds, horses, cattle and primates.

Botulinum toxin complexes are present in form of high-molecular protein complexes comprising two components; namely the paralytically acting neurotoxin component and an associated non-toxic bacterial protein component which can be regarded as a coat protein including hemagglutinin and non-hemagglutinin proteins. The molecular weight of the botulin toxin complexes varies among the distinct botulinum toxin serotypes A, B, $C_1$, $C_2$, D, E, F and G from about 300 kDa to about 900 kDa. With regard to the therapeutic application the coat protein is reported to have no significant function and does not contribute to the neurotoxic properties. The neurotoxin component is expressed as an inactive single-chain precursor (non-cleaved polypeptide) having a molecular weight for all of the known botulinum toxin serotypes of about 150 kDa. This single chain precursor is activated by proteolytic cleavage to generate a disulfide-linked two-chain protein. The about 50 kDa light chain protein contains the catalytic domain and is a zinc-containing metalloproteinase and acts as a zinc-endopeptidase. The about 100 kDa heavy chain protein comprises a translocation domain and a receptor-binding domain. The heavy chain mediates binding to the pre-synaptic cholinergic nerve terminals, in particular to the presynaptic part of the motor end plate or neuromuscular junction, and internalization of the toxin into the cell.

With regard to the before-mentioned, when transported to the neuromuscular junction the receptor-binding domain of the heavy chain provides cholinergic specificity and binds the toxin to the presynaptic receptors. Subsequently, the neurotoxin can enter the neuronal cell via receptor-mediated endocytosis and stays inside the endocytic vesicles of the neuronal cells. Upon acidification of the vesicle, the light chain is translocated into the cytoplasm and split off. The light chain protein is a subsection which acts as zinc-endopeptidase and is able to split different proteins of the vesicle fusion apparatus and prevents the exocytosis of the vesicles. In particular, the light chain toxic moiety is able to cleave one or more of the proteins that form the SNARE protein complex depending on the BoNT serotype, wherein the SNARE complex is formed by SNAP-25, syntaxin and VAMP. The SNARE complex normally fuses with the membrane and thus the neurotransmitter acetylcholine is allowed to leave the cell. By discharging the neurotransmitter acetylcholine in the synaptic cleft, a nerve impulse is transmitted to the muscle, which signals the muscle to contract. As the formation of the SNARE complex is prevented through the cleavage of a protein essentially to from said complex by for example BoNT/A, the acetylcholine release is stopped. Consequently, the transmission between the nerve and muscle is blocked, which finally causes paralysis (botulism).

However, despite of its high toxicity, botulinum toxin has been used as an approved active pharmaceutical ingredient since the beginning of the 1980s, in particular in the treatment of specific motoric disorders, such as eye lid spasm (blepharospasm) or wry neck (torticollis spasmodicus). Additionally, botulinum toxin is used in the field of cosmetic medicine, for example in aesthetical treatment. In addition, the treatment of the *glabella* wrinkles is supposed to further exert psychological effects. In particular, this treatment is reported to reduce the symptoms related to major depressive disorder.

Botulinum neurotoxins are inherently instable, in particular under alkaline conditions. Further, they are reported to be heat-labile. For this purpose commercial botulinum neurotoxins are often stored as vacuum-dried or lyophilized material and often additionally contain excipients, added in order to preserve the botulinum neurotoxin integrity and potency during storage and the potential subsequent reconstitution.

Concerning the above-mentioned medical and cosmetic indications, the botulinum neurotoxin usually has to be administered approximately every 3 months. In order to provide a more desirable dosage regimen, US 2012/014532 A1 suggests depot formulations, wherein the botulinum toxin is supposed to have an increased residency time at a subdermal location. With reference to the Examples, the hyaluronic acid used for the formulations is substantially cross-linked hyaluronic acid prepared from a non-cross-linked hyaluronic acid with a lower molecular weight and a cross-linker such as 1,4-butanediol diglycidyl ether. However, the extend-release formulations suggested above still seem to be improvable in view of their application. In particular, the fillers in the formulation according to US 2012/014532 might remain for a long time at the site of administration.

Thus, it was an objective of the present invention to overcome the above-illustrated drawbacks. In particular, it was an objective of the invention to provide an improved formulation of botulinum neurotoxin which provides an extended duration effect of the botulinum. In particular, a formulation ensuring the absence of residual parts of a former administration at the time of a subsequent administration should be provided. Further, undesirable side effects should be prevented or at least significantly reduced.

The objects of the present invention have been unexpectedly solved by a specific composition comprising (a) botulinum neurotoxin type A and (b) non-crosslinked hyaluronic acid having a weight average molecular weight of 2.5 MDa to 4.5 MDa as well as by specific dosage regimens for said composition.

The inventors found out that the composition of the present invention allows the application of unexpectedly high amounts of botulinum neurotoxin, whereas in conventional botulinum formulations the doses of botulinum toxin cannot be simply enhanced to increase the amount of intake into the cells such that the above effect is achieved. This is because a substantial part of the botulinum toxin is supposed to rapidly reach the systemic circulation via the lymphatic drainage or directly via the venous system. By reaching the systemic circulation, the botulinum might be spread to the adjacent tissue and might cause side effects at the corresponding location. For example, an overdose of a conventional botulinum toxin formulation being injected in the *glabella* wrinkle might result in a drooping eyelid. According to the present invention, now significantly higher amounts of botulinum neurotoxin can be administered without using a depot formulation which remains for days, weeks or months at the site of administration.

SUMMARY OF THE INVENTION

This invention provides a composition comprising (a) botulinum neurotoxin and (b) non-crosslinked hyaluronic acid, preferably having an average molecular weight of 2.5 MDa to 4.5 MDa and/or an intrinsic viscosity from 2.7 to 3.3 m$^3$/kg.

Further, this invention provides the present composition for use in the treatment of dystonia, wherein 220 to 500 units of botulinum neurotoxin are administered, for use in the treatment of spasticity, wherein 500 to 1000 units of botulinum neurotoxin are administered, or for use in the treatment of wrinkles, wherein 40 to 50 units of botulinum neurotoxin are administered.

This invention in addition provides a method for cosmetically smoothing or preventing wrinkles of a mammal, preferably wrinkles being a consequence of extensive mimic activity, wherein said method comprises (i) administering the present composition and (ii) repeating the administration after 4 to 9 months.

Finally, a subject of the present invention is the cosmetic use of the present composition, preferably wrinkles being a consequence of mimic activity, wherein the composition applied comprises 40 to 50 units of botulinum neurotoxin.

BRIEF DESCRIPTION OF THE DRAWINGS

FIG. 1 shows digit abduction scoring of mice injected into the right gastrocnemius muscle with 0.8 ml of the composition according to the Reference Example (squares) or with 1.6 ml of the composition according to Example 1 (bullets).

FIG. 2 shows digit abduction scoring of mice injected into the right gastrocnemius muscle with 0.8 ml of the composition according to the Reference Example (squares) or with 2.5 ml of the composition according to Example 1 (crosses).

DETAILED DESCRIPTION OF THE INVENTION

The composition of the present invention comprises as component (a) botulinum neurotoxin.

In a preferred embodiment component (a) is botulinum neurotoxin type B. (BoNT/B). Botulinum neurotoxin type B shows a catalytic behavior for the cleavage on the vesicle-associated membrane protein 2 (VAMP 2).

In an alternative preferred embodiment component (a) is botulinum neurotoxin type E. (BoNT/E). Botulinum neurotoxin type E also cleaves the 25 kD (kiloDalton) synaptosomal associated protein 25, SNAP-25, but it targets different amino acid sequences within this protein as compared for example to botulinum neurotoxin type A. Botulinum neurotoxin type E comprises eight subtypes, BoNT/E1 to BoNT/E8 and can be present also as recombinant botulinum neurotoxin. Sequence and preparation botulinum neurotoxin type E is e.g. disclosed in WO 2014/068317. In particular reference is made to Seq. ID No. 1, 2 and 3.

In a particular preferred embodiment the composition of the present invention comprises as component (a) botulinum neurotoxin type A.

The botulinum neurotoxin type A complex preferably comprises a neurotoxin component of about 150 kDa, which can be split into the above described light chain (about 50 kDa) and the heavy chain (about 100 kDa) chain and optionally one or more coat proteins such as haemagglutinin or non-haemagglutinin. In a preferred embodiment the botulinum neurotoxin type A complex can have a weight molecular weight of 300 kDa to 900 kDa, especially 300, 600 or 900 kDa. Alternatively preferred the botulinum neurotoxin type A complex comprises the neurotoxin component and further proteins, such as haemagglutinin or non-haemagglutin proteins.

Botulinum neurotoxin type A is considered to be a very toxic compound. The $LD_{50}$-values in mice extend from about 30 pg/kg at intravenous donation to about 3 ng/kg at inhalation. The dosing of the botulinum is related the biological activity and is measured in biological units (E), respectively in mouse units (MU), wherein one biological unit (E) corresponds to one mouse unit (MU). One biological unit (E) corresponds to the amount of toxin injected into the abdomen, wherein the amount is high enough to kill 50% of a group of female Swiss Webster mice, each having a body weight of 18 to 20 grams.

As mentioned above, botulinum neurotoxin type A can be obtained from cultures of *Clostridium botulinum*. The protein can be precipitated from the culture medium and purified by several steps of centrifugation, precipitation and adsorption. The purified toxin can be stored at −70° C. and subsequently defrosted without loss of efficacy of the toxin. A solution of the solid toxin and sterile, isotonic saline can be stored in the refrigerator for at most four hours without losing its potency. This reconstitution can be carried out by adding a specific amount of 0.9% saline to a specific amount of botulinum toxin such that a specific concentration of the botulinum neurotoxin type A per volume is obtained, which is usually metered in units/ml.

In an embodiment the present invention encompasses isoforms, homologs, orthologs and paralogs of botulinum toxin that show at least 50%, at least 60%, at least 70%, at least 80%, at least 90% and up to 60%, up to 70%, up to 80%, up to 90%, up to 100% sequence identity to wild-type botulinum toxin, e.g. wild-type botulinum toxin A. The sequence identity can be calculated by any algorithm suitable to yield reliable results, for example by using the FASTA algorithm (W. R. Pearson & D. J. Lipman PNAS (1988) 85:2444-2448). Sequence identity may be calculated by comparing two polypeptides or two domains such as two LC domains or fragments thereof. Modified and recombinant botulinum toxins are also within the scope of the present invention. The present invention, however, also refers to botulinum toxins, which are chemically modified, e.g. by pegylation, glycosylation, sulfatation, phosphorylation or any other modification, in particular of one or more surface or solvent exposed amino acid(s). The modified, recombinant, isoforms, homologs, orthologs, paralogs and mutants suitable for use in the present invention are biologically active, i.e. able to translocate into neurons and cleave proteins of the SNARE complex (e.g. SNAP25), to exert its muscle paralyzing effects.

The composition of the present invention further comprises hyaluronic acid as component (b). Hyaluronic acid is a glycosaminoglycan which can be represented by the follow structural formula:

Thus, hyaluronic acid can be regarded as a polymer of disaccharides, wherein said disaccharides are composed of two glucose derivatives, namely D-glucuronic acid and D-N-acetylglucosamine. In the disaccharide, glucuronic acid is glycosidically β(1→3)-linked to N-acetylglucosamine which in turn is glycosidically β(1→4)-linked to the next glucoronic acid.

The inventors found that the composition of the present invention should comprise a specific grade of hyaluronic acid. The hyaluronic acid used in the present invention has a rather high molecular weight, wherein the high molecular weight is not achieved by crosslinking but by linear chains having respective lengths.

Generally, in the present invention the hyaluronic acid used as component (b) is a non-crosslinked hyaluronic acid. In a preferred embodiment the hyaluronic acid has an average molecular weight of 2.5 MDa to 4.5 MDa, preferably from 2.7 to 4.2 MDa, more preferably from 3.0 to 4.0 MDa, in particular from 3.3 to 3.8 MDa.

The average molecular weight of the hyaluronic acid was calculated from the determined intrinsic viscosity. Hence, it can be referred to as "viscosity average molecular weight".

The intrinsic viscosity of the hyaluronic acid was measured according to Ph. Eur. 6.0, 2.2.9, using the Ubbelohde capillary viscosimeter at 20° C. and water as solvent. The respective average molecular weight M was calculated according to the Mark-Houwink relationship $[\eta]=KM^a$ wherein η is the intrinsic viscosity, log(K) is the intercept and a the slope. Preferably, for non-crosslinked hyluronic acid a can be set to be 0.7.

In a preferred embodiment the hyaluronic acid (b) can be characterized (instead or in addition to the above mentioned molecular weight) by its intrinsic viscosity. Preferably, the intrinsic viscosity is from 2.7 to 3.3 $m^3/kg$, more preferably from 2.80 to 3.20 $m^3/kg$. still more preferably from 2.90 to 3.15 $m^3/kg$, in particular about 3.09 $m^3/kg$. The viscosity is determined as described above.

It is noted that in the present invention the term "non-crosslinked hyaluronic acid" comprises all the pharmaceutically acceptable salts, hydrates and/or solvates thereof. Preferably, non-crosslinked hyaluronic acid is present in form of the sodium salt.

In a preferred embodiment of the invention, the polydispersity index of the non-crosslinked hyaluronic can be from 1.0 to 5.0, preferably 1.1 to 4.0, more preferably from 1.2 to 3.5, still more preferably from 1.3 to 3.0, especially 1.4 to 2.5, in particular 1.5 to 2.0.

With regard to chemistry, dispersity can be regarded as a dimension of the heterogeneity of sizes of molecules or particles. In a uniform collection, the objects have the same size, shape or mass. The polydispersity index (PDI) or simply dispersity index D, is a measure of the distribution of molecular mass in a given polymer sample and is calculated according to the following formula:

$$PDI=M_w/M_n,$$

wherein

Mw is the weight average molecular weight and $M_n$ is the number average molecular weight.

Mw and $M_n$ both can be determined by gel permeation chromatography (GPC),

In a preferred embodiment the present composition may contain 2 to 4 units, preferably 2.2 to 3.8 units, more preferably 2.4 to 3.6 units of botulinum neurotoxin, preferably of botulinum neurotoxin type A per milligram of non-crosslinked hyaluronic acid.

In an alternative preferred embodiment the present composition may contain 20 to 40 units, preferably 22 to 38 units, more preferably 24 to 36 units of botulinum neurotoxin, preferably of botulinum neurotoxin type A per milligram of non-crosslinked hyaluronic acid.

The composition of the present invention may comprise various other pharmaceutically acceptable substances, for example salts, radical scavenging agents, neurotoxin stabilizing agents, crystallization inhibitors, sugars, amino acids, vitamins, anesthetic agents, surfactants, tonicity modifiers and the like. The term "pharmaceutically acceptable" as used herein refers to those compounds or substances which are suitable for contact with the tissues of mammals, especially humans. The term "comprise" as used herein is intended to encompass both the open-ended term "include" and the closed term "consist (of)".

In an embodiment the composition of the present invention preferably comprises
  c) salt
  d) neurotoxin stabilizing agent
  e) crystallization inhibitor,
  f) buffer and/or
  g) radical scavenging agent.

A salt (c) can be any physiologically acceptable salt, preferably a sodium salt, more preferably sodium chloride.

A neurotoxin stabilizing agent (d) can be regarded as a compound that stabilizes the botulinum neurotoxin, preferably botulinum neurotoxin type A protein, and prevents said protein from degradation. Examples are protein such as Human Serum Albumin (HSA) and gelatin, wherein HSA is preferred.

In an alternative preferred embodiment the present composition does not contain any neurotoxin stabilizing agent, preferably is free of Human Serum Albumin (HSA).

A crystallization inhibitor (e) is a substance that prevents the crystallization of the neurotoxin for example during a lyophilization step. Examples of crystallization inhibitors are sugars, such as glucose, fructose, galactose, trehalose, sucrose and maltose. Preferred are glucose, fructose and sucrose, in particular sucrose.

Buffers (f) are substances which are used to provide a specific pH value when the composition is in from of a solution, preferably an aqueous solution, to achieve a painless application, such as an injection. Preferably, when the composition is in form of an aqueous solution buffers provide a pH value between 6.1 and 7.6, preferably between 6.2 and 7.2, more preferably between 6.3 and 7.1, and in particular between 6.5 and 7.0. Buffers can be for example phosphate buffers, citrate-phosphate buffers, lactate buffers, acetate buffers and the like.

A compound which prevents or slows down the degradation of the botulinum toxin can be regarded as radical scavenging agent (g). Examples of radical scavenging agents are polyols, such as glycerin, and sugar alcohols, such as mannitol, inositol, lactilol, isomalt, xylitol, erythriol and sorbitol.

In a preferred embodiment the present composition does not comprise mannitol.

In an embodiment the present composition can preferably contain:
- a) 20 to 40 units of botulinum neurotoxin, preferably botulinum neurotoxin type A
- b) 2.5 to 9 mg non-crosslinked hyaluronic acid
- c) 3.6 to 20 mg salt, preferably sodium chloride
- d) 0 to 1.5 mg or 0.2 to 1.5 mg neurotoxin stabilizing agent, preferably human serum albumin
- e) 0.4 to 0.94 mg crystallization inhibitor
- f) 0.3 to 0.6 mg buffer, preferably phosphate buffer
- g) 20 to 40 mg radical scavenging agent.

The above-mentioned composition can preferably be in form of a lyophilisate, such that the composition can be stored without loss of efficacy of the botulinum neurotoxin, preferably botulinum neurotoxin type A. The composition comprising lyophilized botulinum neurotoxin, preferably botulinum neurotoxin type A, can be obtained by reconstituting the lyophilisate with sterile saline. The reconstitution is preferably carried out with 0.9% saline, preferably in an amount of 1 ml. The concentration of the an aqueous composition can preferably be in the following ranges
- a) 20 to 40 units of botulinum neurotoxin, preferably botulinum neurotoxin type A per ml
- b) 0.25 to 0.9% w/v hyaluronic acid
- c) 0.36 to 2.0% w/v salt, preferably sodium chloride
- d) 0 to 0.15% w/v or 0.02 to 0.15% w/v neurotoxin stabilizing agent, preferably human serum albumin
- e) 0.04 to 0.094% w/v crystallization inhibitor
- f) 0.03 to 0.06% w/v buffer, preferably phosphate buffer
- g) 2.0 to 4.0% w/v radical scavenging agent.

In an alternative embodiment the present composition can preferably contain:
- a) 200 to 400 units of botulinum neurotoxin, preferably botulinum neurotoxin type A
- b) 2.5 to 9 mg non-crosslinked hyaluronic acid
- c) 3.6 to 20 mg salt, preferably sodium chloride
- d) 0 to 15 mg or 0.2 to 1.5 mg neurotoxin stabilizing agent, preferably human serum albumin
- e) 4 to 9.4 mg crystallization inhibitor
- f) 0.3 to 0.6 mg buffer, preferably phosphate buffer
- g) 200 to 400 mg radical scavenging agent.

The above above-mentioned alternative composition can preferably be in the form of a lyophilisate, such that the composition can be stored without loss of potency of the botulinum neurotoxin, preferably botulinum neurotoxin type A. The composition comprising botulinum neurotoxin, preferably botulinum neurotoxin type A, can be obtained by reconstituting the lyophilisate with sterile saline. The reconstitution is preferably carried out with 0.9% saline, preferably in an amount of 1 ml. The concentration of the an aqueous composition can preferably be in the following ranges
- a) 200 to 400 units of botulinum neurotoxin, preferably botulinum neurotoxin type A per ml
- b) 0.25 to 0.9% w/v hyaluronic acid
- c) 0.36 to 2.0% w/v salt, preferably sodium chloride
- d) 0 to 1.5% w/v or 0.2 to 1.5% w/v neurotoxin stabilizing agent, preferably human serum albumin
- e) 0.4 to 0.94% w/v crystallization inhibitor
- f) 0.03 to 0.06% w/v buffer, preferably phosphate buffer
- g) 20 to 40% w/v radical scavenging agent.

In a preferred embodiment the present composition might comprise two sub-compositions. A first sub-composition can preferably comprise the components a), d, e) and g) in form of a lyophilisate which is reconstituted for use with 0.9% sterile saline. In an alternative preferred embodiment the first sub-composition in form of a lyophilisate is free of Human Serum Albumin (HSA). The second sub-composition can preferably comprise an aqueous solution of components b) and f). Both of the sub-compositions can preferably be combined to obtain the actual composition prior to its application.

In a preferred embodiment the composition of the present invention can be present as a ready-to-use composition, i.e. the present composition can be present in a form which can be directly administered to the patient. In a preferred embodiment the composition can be present in form of a prefilled glass or syringe, wherein the prefilled glass or syringe can preferably be stored at temperature from 0° to 15° C., more preferably from 2 to 10° C.

When in form of a reconstituted solution the present composition can preferably have a dynamic viscosity of 1.5 to 4 Pa·s, preferably 1.7 to 3.8 Pa·s, more preferably 2.0 to 3.0 Pa·s determined at 25° C. and using an oscillation frequency of 1 Hz. This viscosity of the solution allows for example an application by injection through a 25 to 32 gauge needle.

The complex viscosity was determined using an Anton Paar MCR 302 Rheometer. Oscillation frequency was varied from 10 Hz to 0.1 Hz. At 1 Hz and 25° C. a complex viscosity of 2.31-2.45 Pa*s, G' of 8.9485-9.5135 and tan(δ) of 1.279-1.282 were measured.

Further, when in form of a reconstituted solution the present composition can preferably have an osmolality of 200 to 400 milliosmoles per liter, preferably from 250 to 370 milliosmoles per liter, in particular from 270 to 325 milliosmoles per liter. Preferably, the osmolality can be determined according to Ph. Eur 6.0, section 2.2.35.

A further subject of the present invention is the composition of the invention for use in the treatment of dystonia, wherein preferably 200 to 500 units of botulinum neurotoxin, preferably botulinum neurotoxin type A, are administered. More preferably 220 to 480, 240 to 460, 260 to 440, 280 to 420, 300 to 400, 320 to 380 or 340 to 380 units or any combination thereof, e.g. 240 to 380 units, can be used.

Dystonia describes a pathologic state which is characterized by a dysfunction of the tonus of the muscles. Dystonia is considered to be an extrapyramidal hyperkinesia. Dystonia can result in persistent, involuntary contractions of the (skeletal) muscles. This dysfunction is expressed in extreme tensions and misalignment of the body. A dystonia may occur for example due to a genetic defect, as an independent disease pattern (primary dystonia) as well as in line with other diseases (secondary dystonia), such as Morbus Parkinson, or as a result of a stroke. Depending to the grade of spreading, dystonia can be differentiated into three types:
- focal dystonia, wherein just one body part is affected,
- segmental dystonia, wherein more than one body part is affected,
- generalized dystonia, wherein the whole body is affected.

Examples of focal dystonia are laryngeal dystonia (voice dystonia) or cervical dystonia (misalignment of the head/neck) or, wherein cervical dystonia might be also considered as segmental dystonia, blepharospasm (uncontrolled blinking of a lid), oromandibular dystonia (affection of the mouth area and/or masticatory) and spasmodic dysphonia (affection of the vocal cords). An Example of generalized dystonia is the Segawa syndrome, which is characterized by anomalies of the leg positions.

In one embodiment, the present composition for use in the treatment of dystonia is administered parenterally, preferably in form of an injection. Said injection can be preferably carried out in or close to the affected body part, wherein the injection is preferably subcutaneous or intramuscular, in particular intramuscular.

A further subject of the present invention is the composition of the invention for use in the treatment of spasticity, wherein preferably 500 to 1000 units of botulinum neurotoxin, preferably botulinum neurotoxin type A, are administered. More preferably 550 to 950, 600 to 900, 650 to 850 or 700 to 800 units or any combination thereof, e.g. 600 to 850 units, can be used.

Spasticity can be described as an enhanced internal tension of the (skeletal) muscles. The origin for spasticity is a damage of the areas of the central nervous system responsible for motions, wherein these areas are brain and spinal cord, in particular the pyramidal tract of the first motoneuron. The most common reason for spasticity is a hypoxic damage of the motoric brain area by a cerebral infarct. A monospasticity is a spastic paralysis of one muscle or one extremity. Examples of muscles which can be spastically paralyzed are flexor carpi radialis, flexor carpi ulnaris, flexor, digitorium superficalis, flexor digitorium profundis, brachioradialis, biceps *brachialis*, pronator quadratus, pronator *teres*, flexor pollicis longus, flexor pollicis *brevis*, opponens pollicis. A paraspasticiy is characterized by the paralysis of both legs. A hemispasticity describes the paralysis of the extremities of one half of the body or one half of the face (hemifacial spasm). Finally, a tetraspasticity relates to the spastic paralysis of all four extremities, wherein further also the neck and core muscles can be affected.

In one embodiment, the present composition for use in the treatment of spasticity is administered parenterally, preferably in form of an injection. Said injection can be preferably carried out in or close to the affected body part, wherein the injection is preferably subcutaneous or intramuscular, in particular intramuscular.

A further subject of the present invention is the composition of the invention for use in the treatment of wrinkles, wherein preferably 40 to 55 units of botulinum neurotoxin, preferably botulinum neurotoxin type A, are administered. More preferably 42 to 52, 43 to 49, 44 to 48 or 45 to 47 units or any combination thereof, e.g. 43 to 50 units, can be used. The treatment of wrinkles by botulinum toxin may exert psychological effects. In particular, it is reported that people suffering from depressions feel less depressed after the treatment of wrinkles, in particular of the *glabella* wrinkle, by the injection of botulinum toxin.

In one embodiment, the present composition for use in the treatment of wrinkles is administered parenterally, preferably in form of an injection. Said injection can be preferably carried out in or close to the corresponding wrinkles, wherein the *glabella* wrinkle is preferred. The injection is preferably subcutaneous.

A further subject of the present invention is the present composition for use in the treatment of diseases or conditions associated with hyperactive cholinergic innervation of muscles or exocrine glands, wherein 20 to 1500 units, preferably 100 to 800 units of botulinum neurotoxin, preferably botulinum neurotoxin type A, are administered.

The term "hyperactive cholinergic innervation", as used herein, relates to a synapse, which is characterized by an unusually high amount of acetylcholine release into the synaptic cleft. "Unusually high" relates to an increase of, e.g., up to 25%, up to 50% or more with respect to a reference activity which may be obtained, for example, by comparing the release with the release at a synapse of the same type but which is not in a hyperactive state, wherein muscle dystonia may be indicative of the hyperactive state.

"Up to 25%" means, for example, about 1% to about 25%. Methods for performing the required measurements are known in the art.

Exemplary diseases or conditions associated with hyperactive cholinergic innervation of muscles or exocrine glands include e.g. Frey syndrome, crocodile tears syndrome, axillar hyperhidrosis, plantar hyperhidrosis, hyperhidrosis of the head and the neck, hyperhidrosis of the body, rhinorrhea, Parkinson' disease, amyotrophic lateral sclerosis, hypersalivation, drooling, sialorrhea, spastic conditions and palatal myoclonus, myoclonus, myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia, supranuclear gaze palsy, epilepsia partialis continua, planning of spasmodic torticollis operation, abductor vocal cord paralysis, recalcitant mutational dysphonia, upper oesophageal sphincter dysfunction, vocal fold granuloma, stuttering, Gilles de la Tourette syndrome, middle ear myoclonus, protective larynx closure, postlaryngectomy speech failure, protective ptosis, entropion, sphincter Oddi dysfunction, pseudoachalasia, nonachalsia oesophageal motor disorders, vaginismus, postoperative immobilization, tremor, bladder dysfunction, hemifacial spasm, reinnervation dyskinesias, stiff person syndrome, tetanus, prostate hyperplasia, adiposity treatment, infantile cerebral palsy, achalasia and anal fissures.

In one embodiment, the present composition for use in the treatment of diseases or conditions associated with hyperactive cholinergic innervation of muscles or exocrine glands can preferably be administered parenterally, preferably in form of an injection. Said injection can be preferably carried out in or close to the corresponding part of the body. The injection is preferably intramuscular or subcutaneous.

In a preferred embodiment, the composition of the present invention remains at the site of the administration for up to 24 hours after the administration. This means that once administered the composition is removed from the site of injection, degraded and/or metabolized within 24 hours. Further, it is preferred that the composition of the present invention remains at the site of the administration for at least 10 hours after the administration, i.e. in a preferred embodiment the present composition is present at the site of administration for at least 10 hours up to 24 hours, preferably at least 11 hours up to 22 hours, more preferably at least 12 hours up to 20 hours after the administration.

In a preferred embodiment of the present composition the botulinum neurotoxin type A is released within 12 hours after the administration. The release of the botulinum neurotoxin type A from the present composition is at least 50%, i.e. 50% to 100%, preferably at least 60%, more preferably at least 70%, still more preferably at least 80%, especially at least 90% within 12 hours. The release of the botulinum neurotoxin type A from the composition within the above period ensures that the botulinum neurotoxin type A is made available to the corresponding nerve cell without significant loss of efficacy due to systemic removal of the toxin. This means, contrary to the teaching of US 2012/0141532, that the composition of the present invention is not a depot formulation which is kept for weeks or longer at the site of administration. Instead, the present invention is based on the concept that an extended effect of the botulinum neurotoxin is obtained even if the toxin is released within a rather short period of time compared to US 2012/0141532.

In contrast to the present invention, currently available non-extended-release compositions of botulinum are usually applied every 6 to 12 weeks. Such a frequent application of botulinum toxin is generally not desirable, e.g. such a frequent application is reported to create resistances. For example secondary non-responders are reported to occur due to the presence of neutralizing anti-bodies.

Hence, in another preferred embodiment the composition of the present invention is administered in a more advantageous dosage regimen. The composition of the present invention can preferably be administered every four to nine months, preferably every five to seven months, more preferably about every six months. However, compared to the above state of art, the present composition is not based on the formation of a depot from which the botulinum neurotoxin is continually released. Instead, as described above, the botulinum is preferably released within 12 hours from the composition and absorbed by the nerve cells. Further, as also indicated above, after about 24 hours the remaining parts of present composition start to degrade or to be systemically evacuated, such that within a few days there are no parts of the present composition remaining at the administration site.

A further subject of the invention is a method for cosmetically smoothing or preventing wrinkles of a mammal, preferably wrinkles being a consequence of extensive mimic activity, said method comprises
  (i) administering the composition of the present invention and
  (ii) repeating the administration after 4 to 9 months.

Wrinkles can be regarded as a fold, a ridge or a crease in the skin. Wrinkles being a consequence of extensive mimic activity may substantially refer to wrinkles which are visible in the face of the corresponding mammal, preferably a human being. Examples of wrinkles are furrows, glabellar lines, crow's feet, buccal commissures, jaw lines, perioral wrinkles, cheek folds, marionette creases, lip lines, forehead creases, frown lines, bunny lines, nasolabial folds, under eye wrinkles, and chin folds. Step (i) of administering the composition of the present invention can preferably comprise administering the present composition per injection. The injection can be preferably carried out with an injection needle, preferably with an injection needle size of 27 to 35 gauge, preferably of 30 to 33 gauge. The present composition can preferably be injected in or close to site of the corresponding wrinkle(s). The injection can be subcutaneous or intramuscular, in particular subcutaneous. Preferably, the composition of the invention is administered into the frown lines, horizontal lines, crow's feet, perioral folds, mental ceases, popply chin and/or platysmal bands.

The botulinum toxin may be administered on the same day or on a subsequent day of treatment. For example, during a first treatment session a first fraction of the dose may be administered. This first fraction is preferably a suboptimal fraction, i.e. a fraction, which does not remove the wrinkles or skin lines completely. During one or more treatment sessions, the remaining fraction of the total dose may be administered.

Step (ii) of repeating the administration after 4 to 9 months can preferably include administrating the present composition applying the same conditions/devices as described above. By repeating the administration of the present composition a further dose of botulinum is made available to the cells and the corresponding skin preferably remains in a cosmetically smoothed state. In an alternative embodiment the administration is repeated after 5 to 7 or 5 to 8 months.

In a preferred embodiment of the present method the present composition to be administered comprises 40 to 55 units of botulinum neurotoxin, preferably botulinum neurotoxin type A. More preferably 42 to 52, 43 to 49, 44 to 48 or 45 to 47 units or any combination thereof, e.g. 43 to 50 units, can be used. The methods common in the art for smoothing or preventing wrinkles comprise administering about 20 units of the neurotoxin. The use of compositions containing higher amounts of neurotoxin is reported to significantly enhance the risk of undesired side effects such as drooping for example a drooping eye lid. However, in the present method such negative side effects might not be observed and a higher amount of the neurotoxin is made available to the cells resulting in an extended efficacy. Similarly to the explanations given above, in the present cosmetic method the botulinum neurotoxin A preferably is released within 12 hours from the present composition.

A further subject of the present invention is the cosmetic use of the present composition for smoothing or preventing wrinkles, preferably wrinkles being a consequence of mimic activity, wherein the composition applied comprises 40 to 55 units of botulinum neurotoxin, preferably neurotoxin type A. More preferably 42 to 52, 43 to 49, 44 to 48 or 45 to 47 units or any combination thereof, e.g. 43 to 50 units, can be used.

As indicated above, prior art compositions are reported to contain about 20 units of botulinum neurotoxin when cosmetically used for the smoothing or preventing of wrinkles. Through the high amount of 40 to 55 units of botulinum neurotoxin, preferably neurotoxin type A contained in the applied composition more units of botulinum are made available to the corresponding cells and the use of the present composition for the smoothing or preventing of wrinkles ensures an prolonged effect of the neurotoxin applied with the present composition.

The invention can be illustrated by the following examples:

EXAMPLES

1. Preparation of Compositions

Example 1

Two subunits of the composition were prepared.

Subunit 1: A lyophilisate containing 50 units of botulinum neurotoxin type A, 25 mg Human Serum Albumin (HSA) and 1.18 mg sucrose were reconstituted with 1 ml of 0.9% saline.

Subunit 2: A solution containing 1 ml water, 14 mg non-crosslinked hyaluronic acid having an average molecular weight of about 3.8 kD, 34 mg mannitol, 3.0 mg glycerine, 0.6 mg of phosphate buffer was provided.

The subunits were mixed such that one ml of the resulting aqueous composition each contained:

| | | |
|---|---|---|
| Botulinum neurotoxin type A | 25 | units |
| non-crosslinked hyaluronic acid | 7 | mg |
| Human Serum Albumin (HSA) | 0.125 | mg |
| Sucrose | 0.59 | mg |
| Mannitol | 17.0 | mg |
| Glycerine | 1.5 | mg |
| Phosphate buffer | 0.3 | mg |
| Sodium chloride | 4.5 | mg |

Reference Example

The reference composition is obtained as follows: A lyophilisate containing 50 units of botulinum neurotoxin type A, 25 mg Human Serum Albumin (HSA) and 1.18 mg sucrose were reconstituted with 1 ml of 0.9% saline.

Thus, the resulting aqueous composition each contained:

| | | |
|---|---|---|
| Botulinum neurotoxin type A | 50 | units |
| Human Serum Albumin (HSA) | 0.25 | mg |
| Sucrose | 1.18 | mg |
| Sodium chloride | 0.9 | mg |

2. Comparison of Efficacy 2.1 Two groups of 10 mice each were injected into the right gastrocnemius muscle with 0.8 ml of composition according to the reference Example or with 1.6 ml of the composition according to Example 1, both examples containing 40 units of botulinum neurotoxin type A. No mortality was observed in either group. Minor systemic toxicity signs occurred on day 2-10 to the same extent in both groups.

As can be seen from FIG. 1, the maximal score is 4 (DAS score), indicating a complete paralysis of the hind-paw. The time between onset of paralysis and maximum paralysis was one day. The duration of paralysis to reach the EC50 level (DAS score 2) in a mouse was about 12 days for the reference composition and about 30 days for the composition of the present invention. Thus, an unexpected prolongating effect without increasing side effects is provided by the composition of the present invention.

2.2 The comparison according to above item 2.1 is repeated, wherein the mice treated with the present composition were injected with 2.5 ml of the composition according to Example 1, i.e. 62.5 units of botulinum neurotoxin type A. No mortality was observed in either group. Minor systemic toxicity signs occurred on day 2-10 to the same extent in both groups.

FIG. 2 illustrates the prolongating effect provided by the composition of the present invention without increasing side-effects.

The invention claimed is:

1. A composition comprising consisting of:
   a) purified or recombinant botulinum neurotoxin;
   b) sterilized saline; and
   c) non-crosslinked hyaluronic acid having an average molecular weight of 2.5 MDa to 4.5 MDa and an intrinsic velocity of from 2.7 to 3.3 m$^3$/kg,
   wherein said composition is a sterilized composition having a dynamic viscosity from 1.5 to 4 Pa*s when determined at 25° C. using an oscillation frequency of 1 Hz.

2. The composition according to claim 1, wherein the botulinum neurotoxin is botulinum neurotoxin type A.

3. The composition according to claim 1, wherein the polydispersity index of the non-crosslinked hyaluronic acid is 1.1 to 4.0.

4. A formulation consisting of: the composition of claim 1 and one or more of the following:
   a) a salt,
   b) a neurotoxin stabilizing agent,
   c) a crystallization inhibitor,
   d) a buffer, and
   e) one or more radical scavenging agents.

5. The composition according to claim 1 for use in the treatment or prevention of dystonia, wherein the amount of botulinum neurotoxin is 200 to 500 units.

6. The composition according to claim 1 for use in the treatment or prevention of spasticity, wherein the amount of botulinum neurotoxin is 500 to 1000 units.

7. The composition according to claim 1 for use in the prevention or treatment of wrinkles, wherein the amount of botulinum neurotoxin is 40 to 50 units.

8. A method for cosmetically smoothing or preventing wrinkles of a mammal, said method comprising:
   (i) administering the composition according to claim 1 to a subject, and
   (ii) repeating the administration after 4 to 9 months.

9. The method according to claim 8, wherein the amount of botulinum neurotoxin administered to the subject is 40 to 50 units for each administration.

10. The composition according to claim 1, wherein the amount of non-crosslinked hyaluronic acid is at least 0.25 mg.

11. The composition according to claim 1, wherein the amount of botulinum neurotoxin is at least 40 total units.

12. The composition according to claim 1, wherein 20 to 40 units of botulinum neurotoxin per milligram of non-crosslinked hyaluronic acid is in the composition.

13. The composition according to claim 1, wherein 2 to 4 units of botulinum neurotoxin per milligram of non-crosslinked hyaluronic acid is in the composition.

* * * * *